(12) United States Patent
Kinoshita

(10) Patent No.: US 6,422,742 B1
(45) Date of Patent: Jul. 23, 2002

(54) DIFFERENTIAL SCANNING CALORIMETER

(75) Inventor: Ryoichi Kinoshita, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/204,650

(22) Filed: Dec. 2, 1998

(30) Foreign Application Priority Data

Dec. 3, 1997 (JP) .............................................. 9-332903

(51) Int. Cl.[7] ........................ G01N 25/20; G01N 25/18; G01K 17/06

(52) U.S. Cl. .............................. 374/10; 374/31; 374/11

(58) Field of Search ............................... 374/10, 11, 12, 374/13, 29, 30, 39, 43, 44, 31

(56) References Cited

U.S. PATENT DOCUMENTS

| 3,263,484 A | * | 8/1966 | Watson et al. | |
| 5,474,385 A | * | 12/1995 | Readings | 374/11 |
| 5,813,763 A | * | 9/1998 | Plotnikov et al. | 374/11 |

* cited by examiner

*Primary Examiner*—Diego Gutierrez
*Assistant Examiner*—Gail Verbitsky
(74) *Attorney, Agent, or Firm*—Adams & Wilks

(57) ABSTRACT

A sample holder and a reference holder are arranged coaxially. Heat conductors making heat exchange with a heat sink are joined to the heat sink at the same position. The inside diameter of the heat sink can be made close to the diameter of the sample container without spoiling the stability of the baseline that is a feature of heat-flux DSC. The heat capacity of the heat sink can be decreased. Therefore, the response to the temperature as it is elevated and lowered can be improved greatly.

20 Claims, 2 Drawing Sheets

DIFFERENTIAL SCANNING CALORIMETER

BACKGROUND OF THE INVENTION

The present invention relates to novel improvements in a differential scanning calorimeter, which is one kind of thermal analysis instrument for examining changes in physical properties of a material with temperature or time. More particularly, the invention relates to novel improvements in the detector structure of a heat-flux differential scanning calorimeter.

Differential scanning calorimeters (hereinafter referred to as DSCs) are classified into power-consumption DSC and heat-flux DSC according to the method of detecting heat flux. In the power-consumption DSC, a sample holder and a reference holder have respective heaters. The heat fluxes to the sample and to the reference substance are controlled by energization of the heaters. The heat flow is detected from the electric power difference. On the other hand, the heat-flux DSC has a heat sink having relatively large heat capacity. A heat conductor is mounted between the heat sink and the sample holder. Another heat conductor is mounted between the heat sink and the reference holder. Heat flow due to heat exchange is detected as a temperature difference. Generally, the power-consumption DSC has a feature of good heating and cooling response because the sample holders have small heat capacity and are directly heated. On the other hand, heat-flux DSC has a feature of good baseline stability because it has a heat sink (for example, see T. Hatakeyama and F. X. Quinn "Thermal analysis, Fundamentals and Applications to Polymer Science", John Wiley (1994)". A detector structure for the heat-flux differential scanning calorimeter having such features is described by T. Hatakeyama and F. X. Quinn, "Thermal analysis, Fundamentals and Applications to Polymer Science", John Wiley (1994), p. 9, and is constructed as follows.

a) A sample holder and a reference holder are placed on a heat-sensitive disk. The circumference of the disk is coupled to a heat sink and heat exchange is made. The temperature difference is measured at the rear surfaces of the holders.

b) A sample holder and a reference holder are placed at symmetrical positions on the same plane within a heat sink. Heat conductors are mounted between the bottom surface of the heat sink and the holders, respectively. Heat exchange is made. The temperature difference is measured at given positions on the heat conductors.

c) According to a catalog of FP85 (double-decker DSC) of Metler Corporation (Switzerland), two disklike heat conductors are coupled to a cylindrical heat sink in a vertically spaced relation to each other. A sample holder is placed in an upper position, while a reference holder is placed in a lower position. The temperature difference is measured across the rear surfaces of the holders.

The heat-flux DSC is characterized in that the baseline is stable because a heat sink having a large heat capacity is used. However, the large heat capacity deteriorates the heating and cooling response of the heat sink.

A heater is generally wound around the cylindrical heat sink to control the temperature. In order to reduce the heat capacity of the heat sink for improving the heating and cooling response, the diameter of the heat sink is reduced, the height of the cylindrical heat sink is decreased, the thickness of the wall of the heat sink is decreased, the heat sink is made from a material having a small specific heat capacity, or other method is employed.

Silver or copper having good thermal conductivity is often used as the material to provide uniform temperature distribution except in special cases. An appropriate wall thickness is substantially determined by taking account of the mechanical strength and to mitigate pulsation of the heater control. Decreasing the height and the diameter contributes directly to a decrease in the heat capacity. Decreasing the diameter contributes more.

In the DSC where the sample holder and the reference holder are mounted on the same plane as in the prior art techniques a) and b), limitations are imposed on diameter decrease, although this decrease contributes most to decrease in the heat capacity of the heat sink in improving the heating and cooling response. That is, the diameter of the heat sink needs to be at least twice as large as the diameter of the sample container. Where the temperature distribution on the circumference of the heat sink is taken into consideration, it is desired to place the sample holder and the reference holder at symmetrical positions at the closest possible position to the center on the same plane to stabilize the baseline. Hence, it is not desirable to decrease the diameter very much from this point of view. In other words, it is difficult to decrease the heat capacity of the heat sink to improve the heating and cooling response while securing stability of the baseline.

In the structure where the holders are disposed with the two stages of disks as in the prior art technique c), the sample holder can be placed in the center of the circumference of the heat sink. Furthermore, the diameter of the heat sink can be reduced even to near the diameter of the sample container. In this structure, however, the entrance port for the heat flow from the heat sink to the sample holder is spaced in the vertical direction of the cylinder from the entrance port for the heat flow from the heat sink to the reference holder. It is difficult to stabilize the baseline by the effects of the temperature distribution in the vertical direction.

SUMMARY OF THE INVENTION

To solve the foregoing problem, the present invention provides a differential scanning calorimeter comprising, a sample holder on which a sample container is disposed, a reference holder provided symmetrically with respect to a certain plane which is parallel to a sample-disposed plane of the sample holder, a heat sink surrounding both holders, the heat sink being in the shape of a rotation symmetry body having a rotation axis perpendicular to the certain plane, heat conductors coupled to the inner surface of the heat sink crossed by the certain plane and coupled to the ends of both holders so as to make heat exchange between the heat sink and the holders, and temperature detectors coupled to each opposite surface of both holders.

In the heat flow detection mechanism of the structure described above, the entrance port for heat flow going from the heat sink to the sample holder is the same as the entrance port for heat flow going from the heat sink to the reference holder. Therefore, a baseline having good stability can be obtained without being affected by the vertical temperature distribution in the heat sink. Furthermore, the inside diameter of the heat sink can be decreased to near the diameter of the sample container. Note that decreasing the inside diameter of the heat sink contributes most to decrease in the heat capacity of the heat sink in improving the heating and cooling response to the heat sink. The heating and cooling response can be improved dramatically while securing stability of the baseline of the heat-flux DSC.

DETAILED DESCRIPTION OF THE INVENTION

Figure 1:
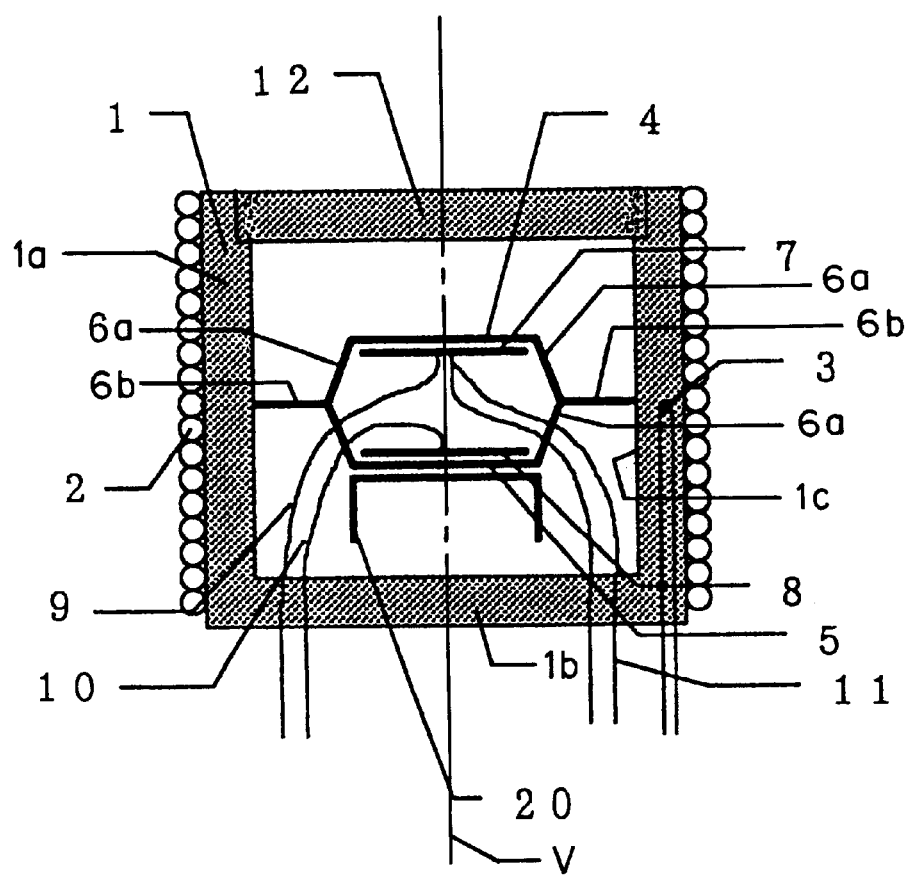
FIG. 1 is a vertical cross section of a differential scanning calorimeter of a structure in accordance with an embodiment of the present invention.

FIG. 1 shows a vertical cross section of a differential scanning calorimeter of the structure in accordance with the embodiment of the present invention.

Indicated by 1 is a cylindrical heat sink of silver having a cylindrical side wall 1a and a closed lower end wall 1b. A cover 12 is removably connected to the open upper end of the cylindrical side wall 1a and constitutes an upper end wall of the heat sink 1. A heater 2 is wound around the heat sink 1. A thermocouple 3 for controlling the temperature of the heat sink 1 is incorporated in the heat sink 1. The temperature of the heat sink 1 is appropriately controlled by a temperature is appropriately controlled by a temperature program and a temperature control circuit (not shown).

A sample holder 4 and a reference holder 5 are at symmetrical positions with respect to a plane. That is, when viewed from above the heat sink 1, the sample holder 4 and the reference holder 5 overlap each other and are identical in shape. As shown in FIG. 1, the holders 4 and 5 are in superposed vertically spaced-apart relation. A set of four heat conductors 6 is joined to the holders 4 and 5 and to the inner surface 1c of the heat sink 1. Heat is transmitted to the holders 4 and 5 through the heat conductors 6. As shown in FIG. 1, each heat conductor 6 has a laterally extending Y-shaped cross section. The diverging upper ends of the Y-shape of the heat conductor 6 constitute diverging arm portions 6a, 6a which are joined at the ends of the holders 4 and 5, respectively. The ends of the heat conductor 6 joined at the ends of the holders 4 and 5 are coupled into a unit. The lower end of the Y-shape of the heat conductor 6 constitutes a leg portion 6b which is joined to the inner surface 1c of the heat sink at substantially the vertical center or mid-point thereof.

Figure 2:
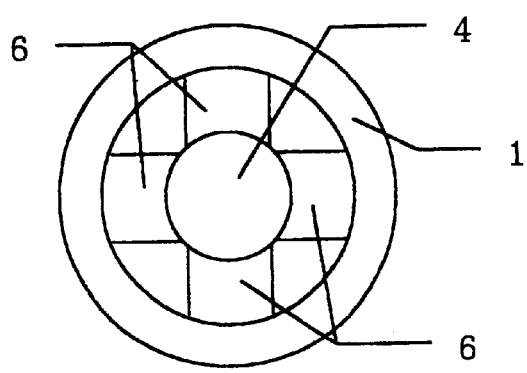
FIG. 2 is a top view of the differential scanning calorimeter in accordance with the embodiment of the invention.

FIG. 2 shows a differential scanning calorimeter (heat sink 1) in accordance with an embodiment of the present invention, taken from above. Heat conductors 6 are joined to the circular sample holder 4 from four directions, and are coupled to the inner surface 1c of the heat sink. Similarly, the heat conductors 6 are joined between the reference holder 5 and the inner surface 1c of the heat sink. The method of coupling can be welding, brazing, or the like. In the illustrative embodiment, the holders 4 and 5 and the heat conductors 6 are integrally made of the same material of constantan. The are brazed to the inner surface of the heat sink. The holders 4, 5 and the heat conductors 6 from a first metal of a thermocouple. In the present embodiment, the heat conductors 6 extend radially in a common place in four directions from the holders 4 and 5 and are connected or coupled to the inner surface of the heat sink 1 at angularly spaced-apart locations lying in the common plane. Heat conductors 6 extending radially in three or two directions may be provided.

The sample holder 4, the reference holder 5, and the heat conductors 6 are formed symmetrically with respect to a horizontal plane at which the heat conductors 6 are joined to the inner surface of the heat sink. Moreover, the holders 4 and 5, the heat conductors 6 and the heat sink 1 are all symmetrical with respect to a vertical center axis V.

Figure 3:
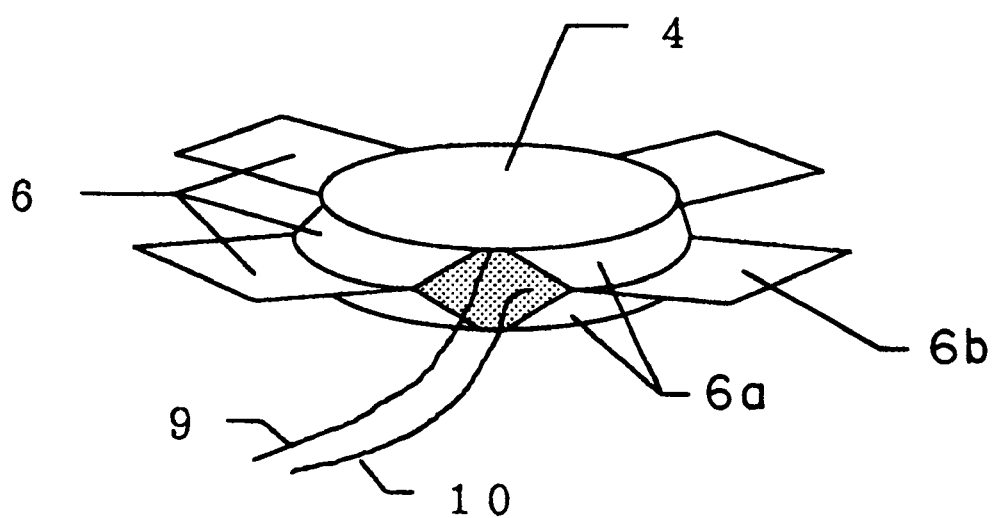
FIG. 3 is a perspective view of a detector portion of the embodiment.

FIG. 3 is a perspective view of the detector portion of the embodiment, especially showing the holders 4, 5 and the portions of the heat conductors 6 integral with the holders 4, 5. Second metal plates 7, 8 of chromel are welded to the rear surfaces of the holders 4, 5, as shown in FIG. 1. Wires of like metal (chromel) are welded as lead wires 9, 10 to the second metal plates 7, 8. The electrical connection between the lead wires 9 and 10 is a chromel-constantan-chromel connection. A signal indicating the temperature difference between the sample holder 4 and the reference holder 5 is produced. The lead wires 9 and 10 are taken from a gap between the sample holder 4 and the reference holder 5 as shown in FIG. 3, passed through the bottom surface of the heat sink 1 via an insulating tube, and taken out. A thermocouple 11 (chromel-alumel) for measuring the temperature of the sample is welded to the rear surface of the sample holder 4, and is taken out through the bottom surface of the heat sink 1 via an insulating tube similarly to the lead wires 9 and 10.

The sample is put into the sample container and placed on the sample holder 4. In the illustrative embodiment, an empty sample container 20 is previously welded or otherwise mounted to the reference holder 5. During measurement, it is not necessary to enter the reference substance.

A cover 12 is made of the same material (silver) as the heat sink 1, and is mounted after installing the sample container. This makes the heat sink (including the cover) symmetrical even in the vertical direction.

The diameter of the sample container usually used in DSC is approximately 5 to 7 mm. In the illustrative embodiment, a container of 5 mm is placed, and the inside diameter of the heat sink is set to 10 mm. Compared with DSC carrying a container having a diameter of 5 mm and having the prior art structure a) or b), the diameter is about ½ to ⅓. If the maximum temperature elevation rate of the prior art DSC is about 100° C./min, it is possible to follow the temperature at a rate that is 3 to 5 times as high as the conventional rate, using a heater of similar wattage. Furthermore, at the cooling, it is possible to follow the temperature at a rate approximately 3 to 5 times as high as the conventional rate. Experimental values obtained from trial instruments indicate that the temperature elevation rate was about 400° C./min and that the temperature drop rate was improved about threefold.

As can be seen from FIG. 1, heat flows into the holders 4 and 5 only from the vertical center of the inner surface of the heat sink. Therefore, the temperature distribution is more uniform. In consequence, a baseline having stability comparable to the prior art a) or b) is obtained.

In the illustrative embodiment, the holders and the heat conductors are integrally fabricated from the same metal. The resultant unit is also used as a thermocouple used for measurement of heat flow. However, similar advantages can be derived by fabricating the heat conductors and the holders from separate materials, attaching appropriate temperature detectors to the rear surfaces of the holders, and measuring the temperature difference between the sample and the reference substance.

An additional feature of the detector structure shown in FIG. 3 is that lead wires can be easily taken out from the gap between the sample holder and the reference holder.

In the illustrative embodiment, the heat conductors 6 extend from the holders in four directions. A different shape may be adopted with equal utility if the conductors extend from the sample holder and from the reference holder symmetrically and if both holders are coupled to the heat sink at the same position. Also, in this case, if gaps permitting lead wires to be taken out are formed in appropriate positions in the heat conductors, the lead wires can be easily taken out.

A sample holder and a reference holder are arranged coaxially. Heat conductors making heat exchange with a heat sink are joined to the heat sink at the same position. Therefore, the inside diameter of the heat sink can be made close to the diameter of the sample container without spoiling the feature of the heat-flux DSC, i.e., stability of the baseline. The heat capacity of the heat sink can be decreased. Consequently, the heating and cooling response of the heat sink can be improved greatly.

What is claimed is:

1. A differential scanning calorimeter comprising: a heat sink having two opposed end walls spaced apart from one another in a vertical direction and a side wall interconnecting the end walls to define an enclosed space; a sample holder disposed within the heat sink for holding a sample substance during use of the calorimeter, a reference holder disposed within the heat sink for holding a reference substance; a plurality of heat conductors connecting the sample holder and the reference holder in spaced-apart superposed relation in the vertical direction and connecting both holders to an inner surface of the side wall of the heat sink to enable heat exchange between the heat sink and both holders; and temperature detectors coupled to the sample holder and the reference holder.

2. A differential scanning calorimeter according to claim 1; wherein the sample holder and the reference holder are symmetrical with respect to a vertical center axis.

3. A differential scanning calorimeter according to claim 1; wherein the heat conductors are symmetrically disposed with respect to a vertical center axis.

4. A differential scanning calorimeter according to claim 1; wherein the heat conductors are connected to the inner surface of the side wall at locations lying in a common plane extending transversely to the vertical direction.

5. A differential scanning calorimeter according to claim 1; wherein the heat conductors each have a leg portion connected at one end thereof to the inner surface of the side wall and connected at the other end thereof to two diverging arm portions, the two diverging arm portions being connected to respective ones of the sample holder and the reference holder.

6. A differential scanning calorimeter according to claim 5; wherein the leg portions of the heat conductors all lie in the common plane.

7. A differential scanning calorimeter according to claim 1; wherein the sample holder, reference holder and heat conductors comprise an integral unit comprised of the same metallic material.

8. A differential scanning calorimeter according to claim 1; wherein one end wall of the heat sink comprises a removable cover removably connected to the side wall.

9. A differential scanning calorimeter according to claim 1; wherein the sample holder and the reference holder are respectively positioned on opposite sides of the common plane.

10. A differential scanning calorimeter according to claim 1; wherein the heat sink, the sample holder, the reference holder and the heat conductors are all symmetrical with respect to a vertical center axis.

11. A differential scanning calorimeter according to claim 10; wherein the heat conductors are connected to the inner surface of the side wall at locations lying in a common plane extending transversely to the vertical center axis.

12. A differential scanning calorimeter according to claim 10; wherein the heat conductors each have a leg portion connected at one end thereof to the inner surface of the heat sink and connected at the other end thereof to two diverging arm portions, the two diverging arm portions being connected to respective ones of the sample holder and the reference holder.

13. A differential scanning calorimeter according to claim 12; wherein the leg portions of the heat conductors all lie in the common plane.

14. A differential scanning calorimeter according to claim 15; wherein the sample holder, reference holder and heat conductors comprise an integral unit comprised of the same metallic material.

15. A differential scanning calorimeter comprising:

a sample holder on which a sample container is disposed during use of the calorimeter;

a reference holder disposed in vertically spaced-apart superposed relation with respect to the sample holder;

a cylindrical heat sink surrounding both holders;

heat conductors coupled to an inner surface of the heat sink and coupled to the ends of both holders to support the holders in vertically spaced-apart superposed relation within the heat sink and to effect heat exchange between the heat sink and the holders; and temperature detectors coupled to opposite surfaces of both holders.

16. A differential scanning calorimeter according to claim 15; wherein the sample holder, reference holder, and heat conductors are made of a first metallic material; and further comprising a second metallic material coupled to opposite surfaces of both holders to form a thermocouple; and lead wires made of the second metallic material to detect a difference in temperature between the sample holder and the reference holder.

17. A differential scanning calorimeter according to claim 15; wherein the heat conductors are formed symmetrically with respect to both holders.

18. A differential scanning calorimeter according to claim 15; wherein each heat conductor has a generally Y-shaped cross section.

19. A differential scanning calorimeter according to claim 18; wherein a part of each heat conductor extends radially and is coupled to the inner surface of the heat sink.

20. A differential scanning calorimeter according to claim 15; further including sample container mounted to the reference holder.

* * * * *